United States Patent
Mokelke et al.

(10) Patent No.: US 8,983,611 B2
(45) Date of Patent: Mar. 17, 2015

(54) NEURAL CONTROL OF CENTRAL SLEEP APNEA

(71) Applicant: Cardiac Pacemakers, Inc., St. Paul, MN (US)

(72) Inventors: Eric A. Mokelke, White Bear Lake, MN (US); Yi Zhang, Plymouth, MN (US); John D. Hatlestad, Maplewood, MN (US); Kenneth C. Beck, Liberty, UT (US); Viktoria A. Averina, Roseville, MN (US); Jon Peterson, Mahtomedi, MN (US); Kent Lee, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 211 days.

(21) Appl. No.: 13/626,399

(22) Filed: Sep. 25, 2012

(65) Prior Publication Data
US 2013/0079842 A1    Mar. 28, 2013

Related U.S. Application Data

(60) Provisional application No. 61/539,728, filed on Sep. 27, 2011.

(51) Int. Cl.
*A61N 1/00* (2006.01)
*A61N 1/36* (2006.01)

(52) U.S. Cl.
CPC .......... *A61N 1/3611* (2013.01); *A61N 1/36053* (2013.01)
USPC ................................... 607/42; 607/2; 607/62

(58) Field of Classification Search
USPC ................................. 607/2, 42, 62
See application file for complete search history.

(56) References Cited

U.S. PATENT DOCUMENTS

| 4,830,008 A | 5/1989 | Meer |
| 5,123,425 A | 6/1992 | Shannon, Jr. et al. |

(Continued)

FOREIGN PATENT DOCUMENTS

| WO | WO-2009140636 A2 | 11/2009 |
| WO | WO-2009140636 A3 | 11/2009 |

(Continued)

OTHER PUBLICATIONS

Fairbanks, David W., "Neurostimulation for Obstructive Sleep Apnea: Investigations", ENT Journal Jan. 1993 vol. 72, No. 1, (Jan. 1993), 52-57.

(Continued)

*Primary Examiner* — Michael Kahelin
*Assistant Examiner* — Mallika D Fairchild
(74) *Attorney, Agent, or Firm* — Schwegman Lundberg & Woessner, P.A.

(57) ABSTRACT

An apparatus comprises a physiologic sensing circuit and a control circuit. The physiologic sensing circuit is configured to sense an electrical respiration signal representative of respiration of a subject. The control circuit includes a respiration monitor circuit and a therapy circuit. The respiration monitor circuit is configured to extract a respiration parameter from the respiration signal and detect that a value of the respiration parameter is outside of a target value range for the respiration parameter. The therapy circuit is configured to deliver neural stimulation to the carotid sinus of the subject to stimulate respiration and to adjust respiration to maintain the value of the respiration parameter within the target value range.

20 Claims, 8 Drawing Sheets

(56) References Cited

U.S. PATENT DOCUMENTS

| | | | |
|---|---|---|---|
| 5,158,080 | A | 10/1992 | Kallok |
| 5,335,657 | A | 8/1994 | Terry, Jr. et al. |
| 5,504,731 | A | 4/1996 | Lee et al. |
| 5,504,732 | A | 4/1996 | Gregg et al. |
| 5,504,733 | A | 4/1996 | Nakamichi |
| 5,522,862 | A | 6/1996 | Testerman et al. |
| 5,540,731 | A | 7/1996 | Testerman |
| 5,540,732 | A | 7/1996 | Testerman |
| 5,540,733 | A | 7/1996 | Testerman et al. |
| 5,549,655 | A | 8/1996 | Erickson |
| 5,591,216 | A | 1/1997 | Testerman et al. |
| 6,021,352 | A | 2/2000 | Christopherson et al. |
| 6,076,015 | A | 6/2000 | Hartley et al. |
| 6,251,126 | B1 | 6/2001 | Ottenhoff et al. |
| 6,266,564 | B1 | 7/2001 | Hill et al. |
| 6,269,269 | B1 | 7/2001 | Ottenhoff et al. |
| RE38,705 | E | 2/2005 | Hill et al. |
| 6,928,324 | B2 | 8/2005 | Park et al. |
| 7,155,278 | B2 | 12/2006 | King et al. |
| 7,189,204 | B2 | 3/2007 | Ni et al. |
| 7,336,996 | B2 | 2/2008 | Hartley et al. |
| 7,469,697 | B2 | 12/2008 | Lee et al. |
| 7,591,265 | B2 | 9/2009 | Lee et al. |
| 7,596,413 | B2 | 9/2009 | Libbus et al. |
| 7,644,714 | B2 | 1/2010 | Atkinson et al. |
| 7,650,189 | B1 | 1/2010 | Park et al. |
| 7,680,537 | B2 | 3/2010 | Stahmann et al. |
| 7,720,541 | B2 | 5/2010 | Stahmann et al. |
| 7,747,323 | B2 | 6/2010 | Libbus et al. |
| 7,766,842 | B2 | 8/2010 | Ni et al. |
| 7,787,946 | B2 | 8/2010 | Stahman |
| 7,797,050 | B2 | 9/2010 | Libbus et al. |
| 7,809,442 | B2 | 10/2010 | Bolea et al. |
| 7,938,782 | B2 | 5/2011 | Stahmann et al. |
| 2002/0049479 | A1 | 4/2002 | Pitts |
| 2004/0111139 | A1 | 6/2004 | McCreery |
| 2006/0282131 | A1 | 12/2006 | Caparso et al. |
| 2007/0150006 | A1 | 6/2007 | Libbus et al. |
| 2007/0173893 | A1 | 7/2007 | Pitts |
| 2008/0021507 | A1 | 1/2008 | Libbus et al. |
| 2008/0103545 | A1 | 5/2008 | Bolea et al. |
| 2010/0070004 | A1 | 3/2010 | Hlavka et al. |
| 2010/0125310 | A1 | 5/2010 | Wilson et al. |
| 2010/0139667 | A1 | 6/2010 | Atkinson et al. |
| 2010/0174341 | A1 | 7/2010 | Bolea et al. |
| 2011/0071591 | A1 | 3/2011 | Bolea et al. |
| 2011/0093032 | A1 | 4/2011 | Boggs et al. |
| 2011/0106207 | A1 | 5/2011 | Cauller et al. |
| 2011/0106219 | A1 | 5/2011 | Cauller et al. |

FOREIGN PATENT DOCUMENTS

| | | |
|---|---|---|
| WO | WO-2010039853 A1 | 4/2010 |
| WO | WO-2010059839 A2 | 5/2010 |
| WO | WO-2010117810 A1 | 10/2010 |

OTHER PUBLICATIONS

Haxhiu, M. A., et al., "Nonvagal Modulation of Hypoglossal Neural Activity", Original Paper—Respiration 1992; 59, (Jan. 23, 1992), 65-71.

Marzec, M., et al., "Effects of vagus nerve stimulation on sleep-related breathing in epilepsy patients", Epilepsia, 44(7), (Jul. 2003), 930-935.

Miki, H., et al., "Effect of Electrical Stimulation of Genioglossus Muscle on Upper Airway Resistance in Anesthetized Dogs", Tohoku J. exp. Med., 153, (1987), 397-398.

Miki, H., et al., "Effects of Electrical Stimulation of the Genioglossus on Upper Airway Resistance in Anesthetized Dogs", American Review of Respiratory Disease, 140(5), (Nov. 1989), 1279-1284.

Miki, Hiroshi, et al., "Effects of Submental Electrical Stimulation during Sleep on Upper Airway Patency in Patients with Obstructive Sleep Apnea", 1285-1289.

Okada, Yasumasa, et al., "Electrical stimulation of the rabbit pulmonary artery increases respiratory output", Respiratory Physiology & Neurobiology 140, (2004), 209-217.

Ruch, T. C., et al., "Section II—Respiration, The Chemical Regulation of Ventilation", Physiology and Biophysics II, Circulation, Respiration, and Fluid Balance, (1974) 378-392.

Schwartz, Alan D., et al., "Effect of Electrical Stimulation of the Hypoglossal Nerve on Airflow Mechanics in the Isolated Upper Airway", American Review of Respiratory Disease vol. 147, 1993, 1144-1150.

NEURAL CONTROL OF CENTRAL SLEEP APNEA

CLAIM OF PRIORITY

This application claims the benefit of priority under 35 U.S.C. §119(e) of Mokelke et al., U.S. Provisional Patent Application Ser. No. 61/539,728, filed on Sep. 27, 2011, the benefit of priority of which is claimed hereby, and is incorporated by reference herein in its entirety.

BACKGROUND

Implantable medical devices (IMDs) include, among other things, cardiac function management (CFM) devices such as implantable pacemakers, implantable cardioverter defibrillators (ICDs), cardiac resynchronization therapy devices (CRTs), and devices that include a combination of such capabilities. The devices can be used to treat patients or subjects using electrical or other therapy, or to aid a physician or caregiver in patient diagnosis through internal monitoring of a patient's condition. Other examples of IMDs include implantable diagnostic devices, implantable drug delivery systems, or implantable devices with neural or neuro-stimulation capability. The devices may include one or more electrodes in communication with one or more sense amplifiers to monitor electrical heart activity within a patient, and often include one or more sensors to monitor one or more other internal patient parameters. Neural stimulation devices can be used to treat hypertension and respiratory disorders.

OVERVIEW

This document discusses examples of techniques for generating and delivering neural stimulation therapy to affect respiration. An apparatus example includes a physiologic sensing circuit and a control circuit. The physiologic sensing circuit is configured to sense an electrical respiration signal representative of respiration of a subject. The control circuit includes a respiration monitor circuit and a therapy circuit. The respiration monitor circuit is configured to extract a respiration parameter from the respiration signal and detect that a value of the respiration parameter is outside of a target value range for the respiration parameter. The therapy circuit is configured to deliver neural stimulation to the carotid sinus of the subject to stimulate respiration and to adjust respiration to maintain the value of the respiration parameter within the target value range.

This section is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

This document discusses devices and methods for generating and delivering pacing therapy and neural stimulation therapy. Specifically, devices and methods for providing both pacing therapy and neural stimulation therapy via the same circuit are described.

An implantable medical device (IMD) may include one or more of the features, structures, methods, or combinations thereof described herein. For example, a cardiac stimulator may be implemented to include one or more of the advantageous features or processes described below. It is intended that such a stimulator or other implantable or partially implantable device need not include all of the features described herein, but may be implemented to include selected features that provide for unique structures or functionality. Such a device may be implemented to provide a variety of therapeutic or diagnostic functions.

Baroreflex is a reflex triggered by stimulation of a baroreceptor. A baroreceptor includes any sensor of pressure changes, such as sensory nerve endings in the wall of the auricles of the heart, vena cava, aortic arch and carotid sinus, that is sensitive to stretching of the wall resulting from increased or decreased pressure. Clusters of nerve cells can be referred to as autonomic ganglia. These nerve cells can also be electrically stimulated to induce a baroreflex, which inhibits the sympathetic nerve activity and stimulates parasympathetic nerve activity. Autonomic ganglia thus forms part of a baroreflex pathway. Afferent nerve trunks, such as the vagus, aortic and carotid nerves, leading from the sensory nerve endings also form part of a baroreflex pathway.

Figure 1:
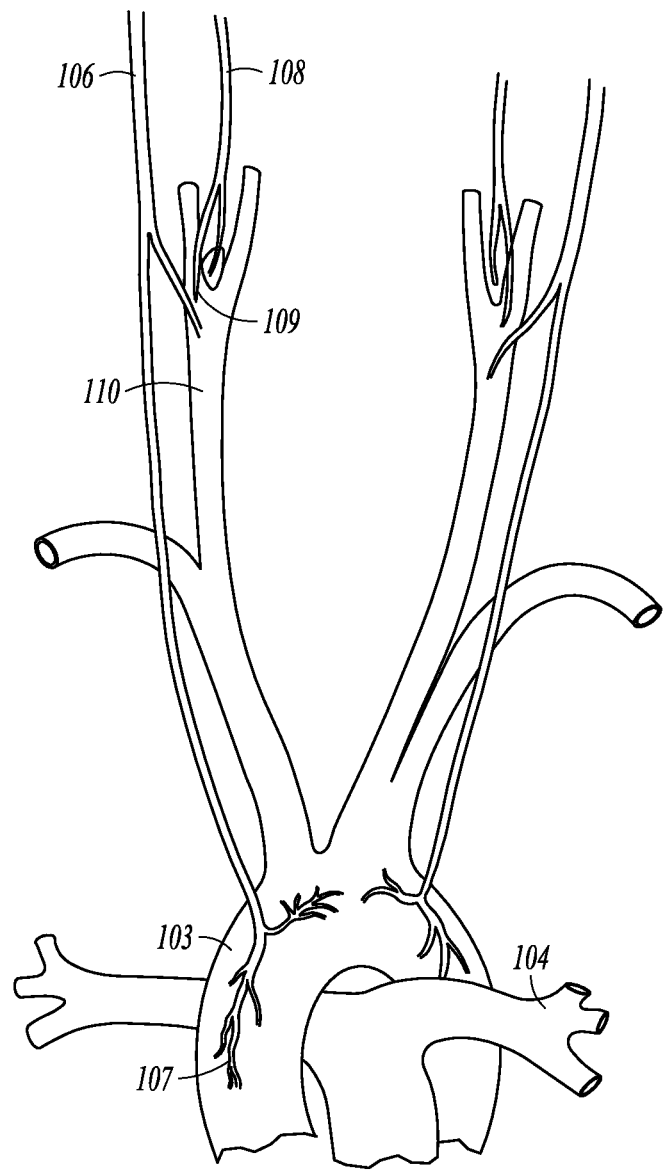
FIG. 1 is an illustration of baroreceptors in the area of the carotid artery, aortic arch, and pulmonary artery.

FIG. 1 illustrates baroreceptors in the area of the carotid artery 110, aortic arch 103, and pulmonary artery 104. Also illustrated are the vagus nerve 106 and the glossopharyngeal nerve 108. Cuffs or collars can be placed around afferent nerve trunks, such as the vagus nerve, leading from baroreceptors to vasomotor centers to stimulate the baroreflex. Activation of sensory nerve endings 107 and 109 can reduce pressure and treat hypertension. Activation of the phrenic nerve (not shown) can be used to artificially stimulate ventilation of a patient or subject.

Figure 2:
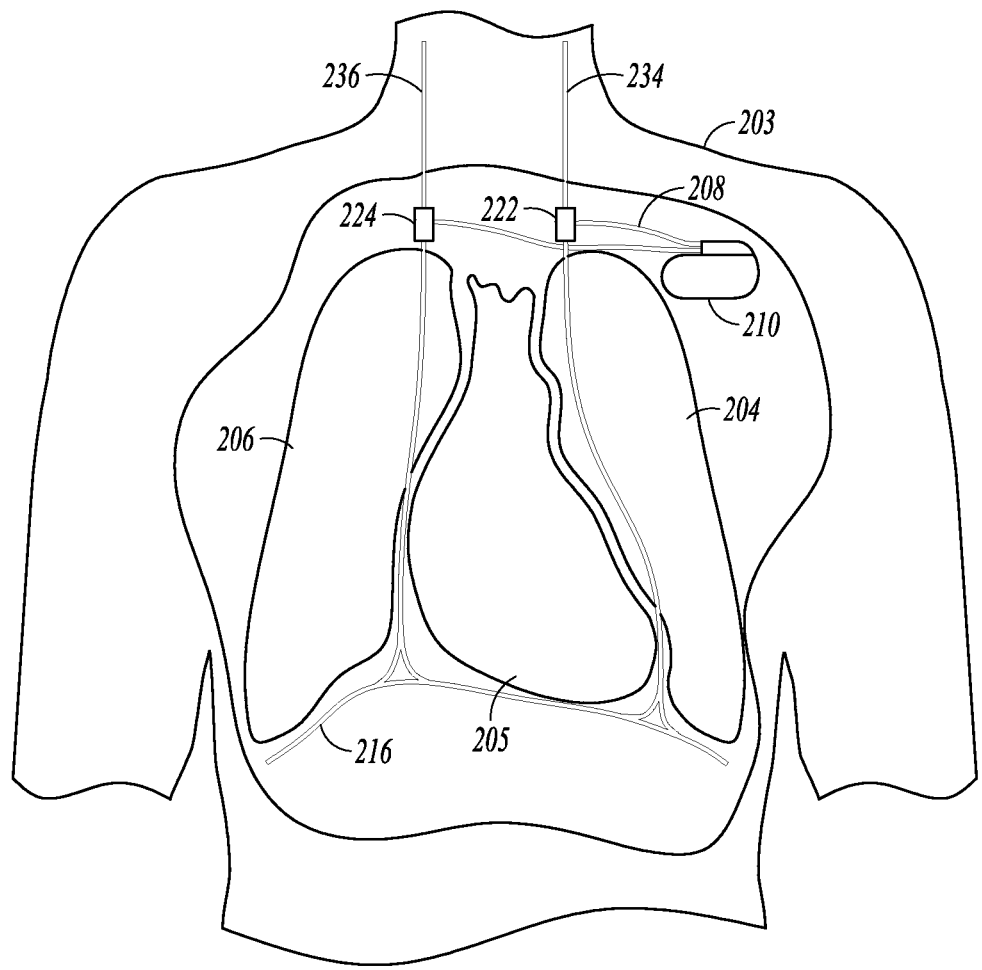
FIG. 2 is an illustration of an example of an IMD implanted in a thorax region of a patient.

FIG. 2 is an illustration of an example of an IMD 210 implanted in a thorax region of a patient 203. The illustration shows the heart 205 of the subject as well as the left lung 204 and right lung 206. Also shown are representations of the left phrenic nerve 234 and right phrenic nerve 236. The IMD 210 is shown implanted in the pectoral region of the patient 203. In the example, the IMD 210 is coupled to one or more subcutaneous leads 208. In certain examples, the lead 208 includes one or more over-the-nerve collars 222 and 224 containing electrodes for contacting a phrenic nerve. In certain examples, the lead 208 includes one or more patch electrodes for contacting a phrenic nerve. In certain examples, the lead 208 is a transvenous lead. The transvenous lead is placed in a vein in proximity to the phrenic nerve to stimulate the phrenic nerve. The IMD 210 provides electrical stimulation to either the right or left phrenic nerve or both the right and left phrenic nerves to artificially induce ventilation. Examples of devices to artificially induce respiration can be found in Caparso et al., "System for Neural Control of Respiration," U.S. Patent Application Publication No. US 2006/0282131, filed Jun. 13, 2005, which is incorporated herein by reference in its entirety.

Figure 3A:
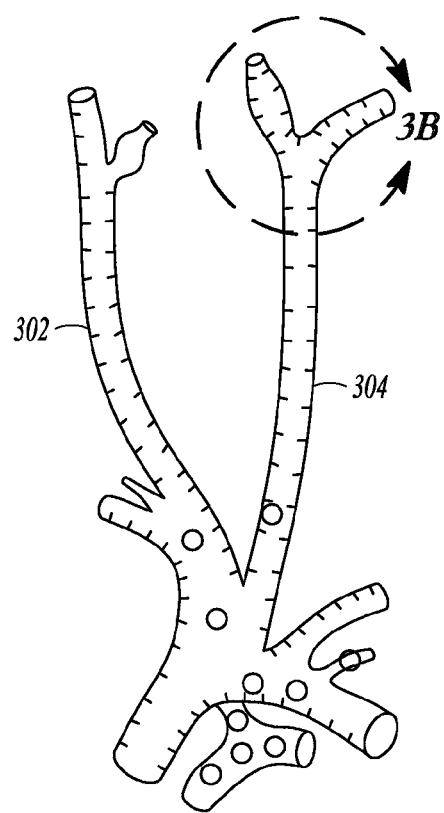
FIGS. 3A and 3B illustrate an internal carotid artery and external carotid artery.
Figure 3B:
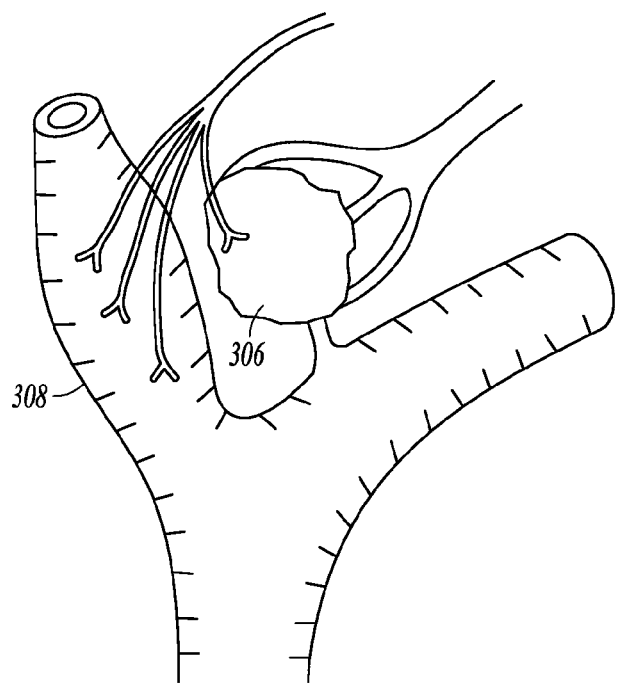

FIGS. 3A and 3B illustrate an internal carotid artery 302 and external carotid artery 304. Also illustrated are representations of the carotid body 306 and carotid sinus 308. The carotid body 306 is a small cluster of chemoreceptors located near the fork or bifurcation of the external carotid artery 304 that runs along both sides of the throat. A chemoreceptor, sometimes referred to as a chemosensor, is a sensory receptor that changes a chemical signal into an action potential. Stated another way, a chemoreceptor changes a chemical stimulus into a stimulus to the autonomic nervous system. Chemoreceptors of the carotid body 306 detect changes in the concentration of arterial blood flow through the carotid body 306. The chemoreceptors of the carotid body 306 are mainly sensitive to changes in partial pressure of oxygen and carbon dioxide. The chemoreceptors are also sensitive to changes in pH and temperature. Changes in partial pressure of carbon dioxide can cause neural action potentials that influence respiration.

A carotid baroreceptor is distinct from a carotid chemoreceptor. Carotid baroreceptors are mechanoreceptors located in the carotid sinus 308, and are near but separate from the carotid body 306. The baroreceptors detect changes in blood pressure that are transmitted through the advential wall. The baroreceptors are the terminal ends of the carotid branch of the glossopharyngeal nerve (e.g., cranial nerve IX). The carotid baroreceptors of the carotid sinus 308 are separate and distinct from the carotid body. However, stimulation of the carotid baroreceptors of the carotid sinus 308 can be used to alter respiration of a subject.

Patients with HF often exhibit some form of apnea or hypopnea. Apnea refers to the condition where external breathing ceases. Hypopnea refers to the condition where external breathing is overly shallow. Sleep apnea refers to cessation of breathing while a patient is sleeping and can be either obstructive or central. Obstructive sleep apnea occurs due to an obstruction of the airway and is usually associated with obesity. Central sleep apnea occurs when the brain stops giving a signal to breathe. It is estimated that 30-50% of HF patients experience some degree of central apnea.

Hyperpnea refers to an increased depth of breathing when required to meet metabolic need of the patient. Hyperpnea may follow a period of central sleep apnea when the patient is aroused from sleep due to the lack of respiration. This can result in oscillation of respiration between apnea and hyperpnea, or Cheyne-Stokes respiration.

Figure 4:
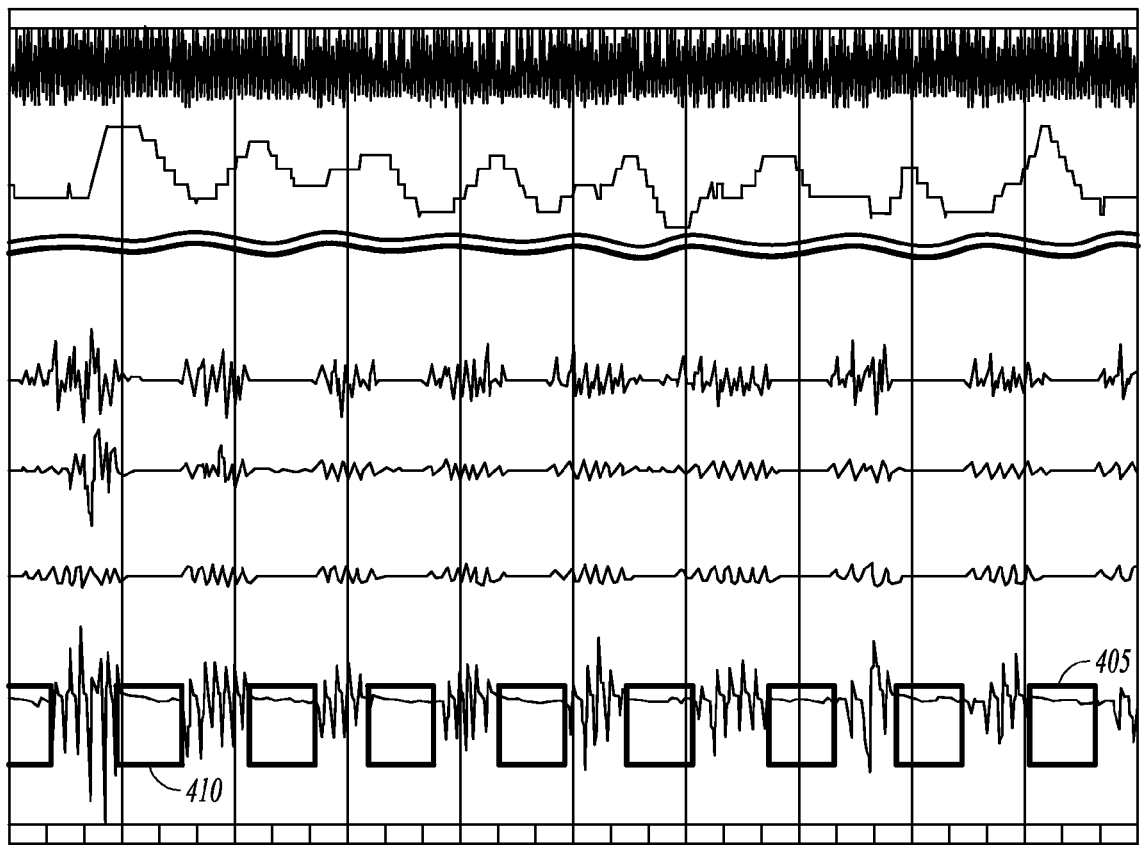
FIG. 4 shows an example of recorded abnormal breathing.

FIG. 4 shows an example of recorded abnormal breathing. Respiration is shown in the waveform 405 of the bottom row. The waveform shows oscillation of respiration between apnea (shown by the squares 410) with episodes of hyperpnea between the episodes of apnea. Partial pressure of carbon dioxide ($pCO_2$) in the bloodstream is a major driver of respiration. Cheyne-Stokes breathing is due to oscillating levels of $pCO_2$.

Figure 5:
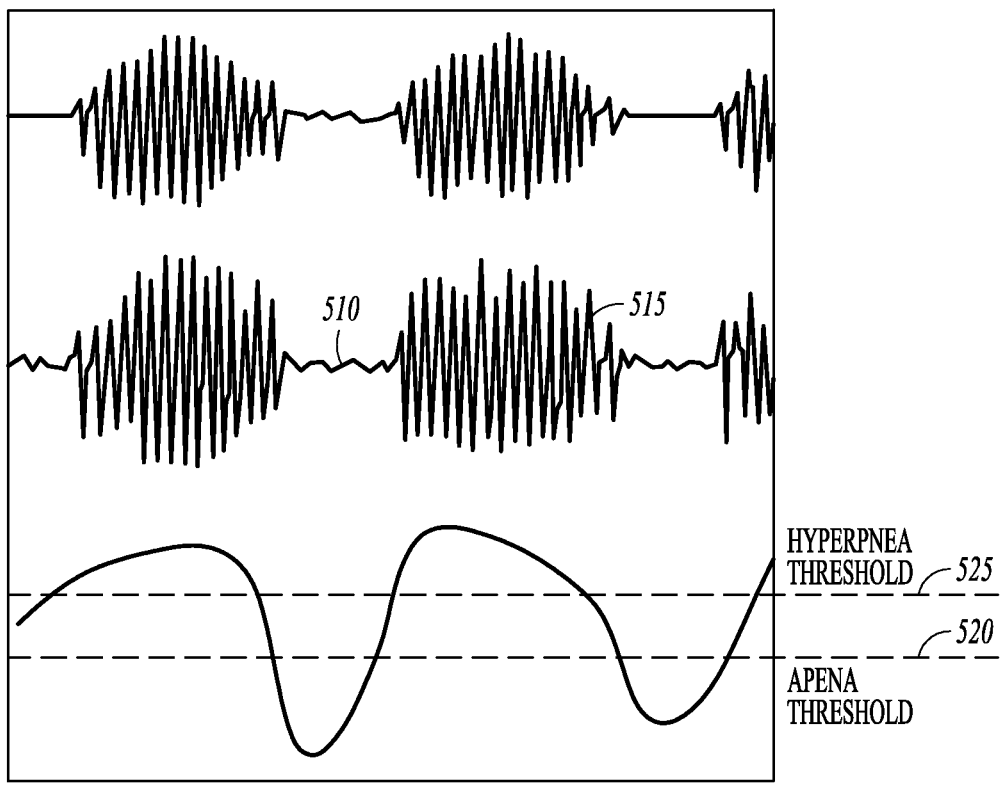
FIG. 5 shows a representation of Cheyne-Stokes breathing and levels of $pCO_2$.

FIG. 5 shows a representation of Cheyne-Stokes breathing and levels of $pCO_2$. Low levels of $pCO_2$ result in episodes of apnea 510 and high levels of $pCO_2$ result in episodes of hyperventilation or hyperpnea 515. The Figure also shows thresholds of $pCO_2$ for apnea 520 and $pCO_2$ threshold for hyperpnea 525. Normal respiration would have $pCO_2$ that stays within the apnea and hyperpnea thresholds.

Figure 6:
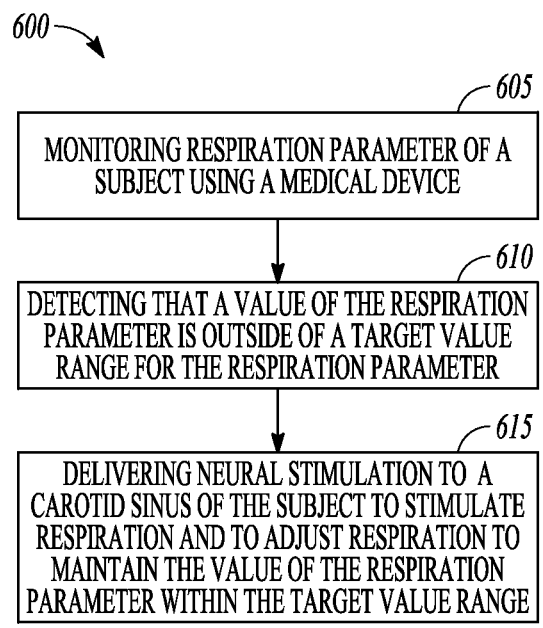
FIG. 6 shows a flow diagram of an example of a method for inducing or stimulating ventilation in a subject.

FIG. 6 shows a flow diagram of an example of a method 600 for inducing or stimulating ventilation in a subject. At block 605, a respiration parameter of a subject is monitored using a medical device. Examples of the respiratory parameter include, among other things, a respiratory rate, respiratory tidal volume, $pCO_2$, minute ventilation, a measure of Cheynes-Stokes breathing and a measure of periodic breathing.

At block 610, a value of the respiration parameter is detected that is outside of a target value range for the respiration parameter. In some examples, the target range of the respiratory parameter targets or represents normal respiration of the subject.

At block 615, neural stimulation is delivered to a carotid sinus of the subject to stimulate respiration and to adjust respiration to maintain the value of the respiration parameter within the target value range. For instance, neural stimulation may be provided to the carotid sinus when the respiration of the subjected is depressed (e.g., hypopnea) or ceases (e.g., apnea). The respiratory parameter may drop outside (e.g., below) the target range of the parameter and neural stimulation can be delivered to the carotid sinus to restore the respiratory parameter to the range of target values (or to a specified target value).

In another example, neural stimulation may be provided when the subject experiences hyperventilation (e.g., hyperpnea). This may also cause the respiratory parameter to be outside (e.g., above) the target value range. Stimulation of the vagal nerve can cause depression of the respiratory system. Thus, neural stimulation can be delivered to the vagal nerve to restore the respiratory parameter to the range of target values. By this method 600, feedback can be used to prevent overshoot or undershoot of the respiration parameter and maintain normal respiration for the patient.

Figure 7:
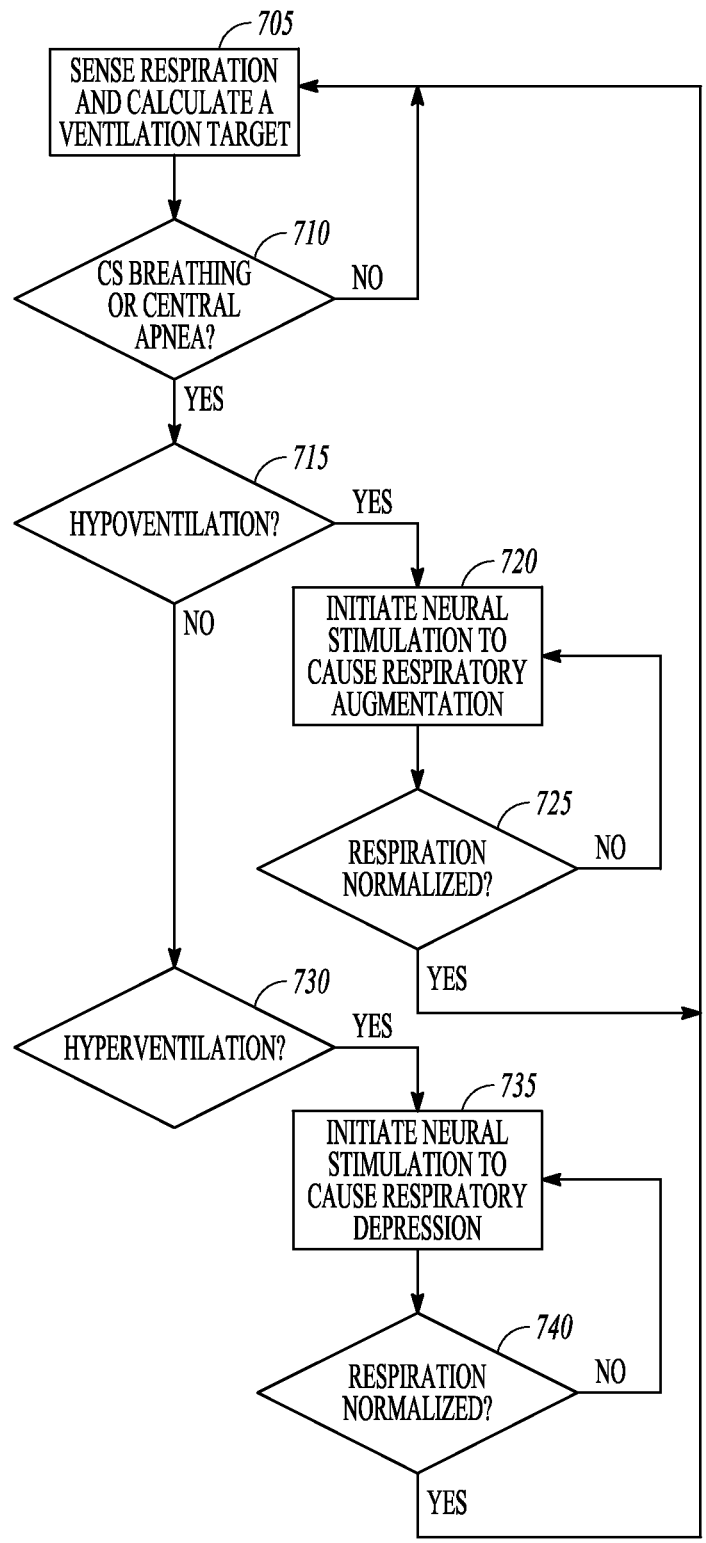
FIG. 7 shows a flow diagram of an example of a method of operating a medical device to use feedback to control respiration of a subject.

FIG. 7 shows a flow diagram of an example of a method 700 of operating a medical device to use feedback to control respiration of a subject. At block 705 respiration of the subject is sensed and a target value for ventilation is calculated. In some examples, the ventilation target is a target value for a respiratory parameter (e.g., respiratory rate, tidal volume, etc.) or a target value range for the parameter.

At block 710, it is determined whether the sensed breathing indicates one or both of Cheyne-Stokes breathing and central apnea. If the breathing indicates hypoventilation at block 715, neural stimulation is initiated at block 720 that augments respiration, such as by stimulation of the carotid sinus. If respiration has normalized (e.g., the respiratory parameter is within the target range) at block 725, the method returns to sensing respiration at block 705. Otherwise, the stimulation is maintained.

At block 730, it is determined whether the sensed breathing indicates hyperventilation. If the breathing indicates hyperventilation at block 730, neural stimulation is initiated at block 735 that depresses respiration, such as by stimulation of the vagal nerve. If respiration has normalized (e.g., the respiratory parameter is within the target range) at block 740, the method returns to sensing respiration at block 705. Otherwise, the stimulation is maintained.

Figure 8:
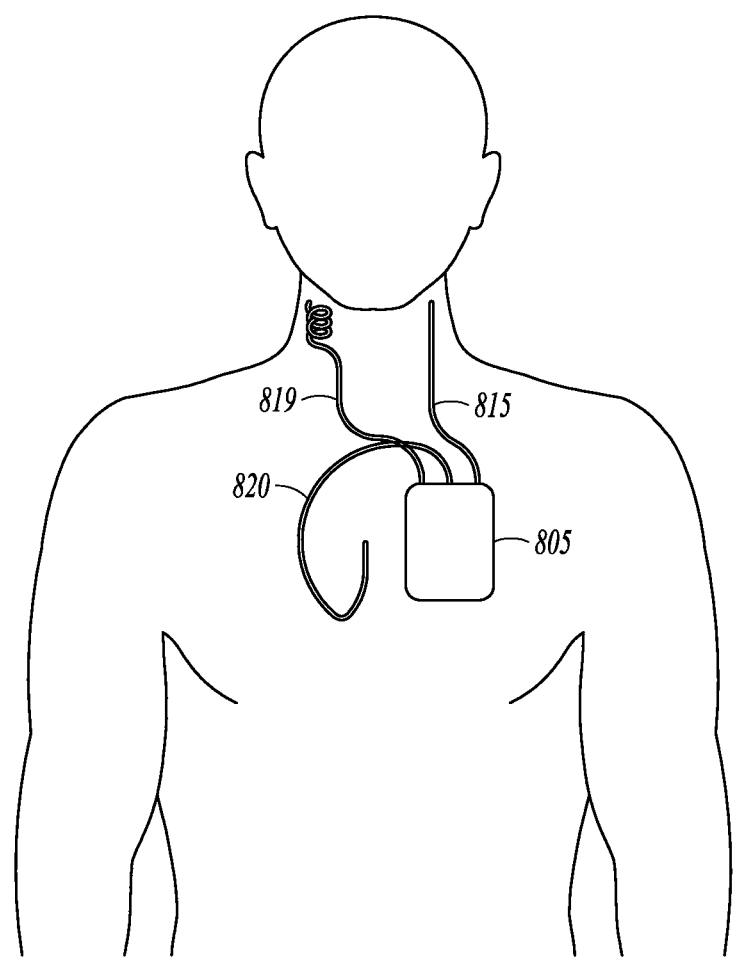
FIG. 8 is an illustration of a system that uses an implantable medical device.

FIG. 8 is an illustration of a system that uses an implantable medical device (IMD 805). The system also includes a carotid sinus lead 810 and a vagal lead 815. In some examples, the system also includes a pulmonary artery lead 820. The IMD 805 includes a sensor (not shown) to provide a sensor signal representative of respiration of the subject. Stimulation to the carotid sinus by the carotid sinus lead 810 and stimulation to the vagal nerve by the vagal lead 815 provide the neural stimulation to implement feedback to control respiration of a subject. The pulmonary artery lead 820 can be used to induce inspiration by stimulating chemosensors together with the stimulation of the carotid sinus.

Figure 9:
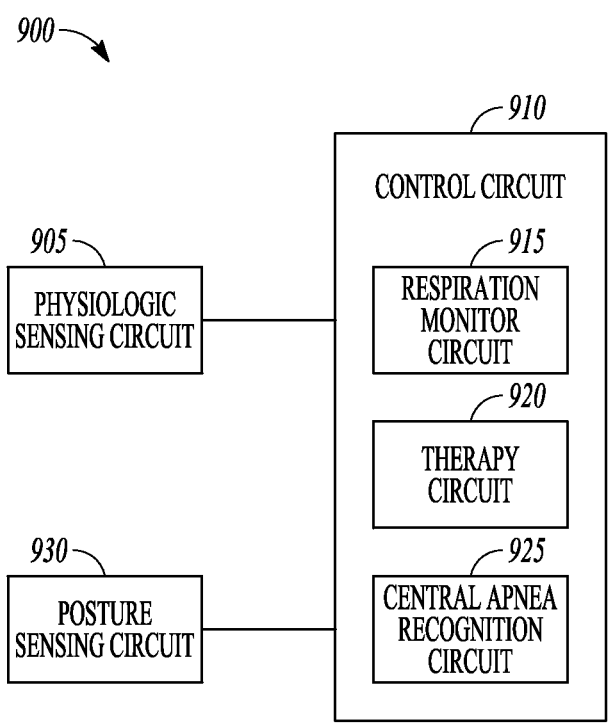
FIG. 9 is a block diagram of portions of an example of an ambulatory medical device to deliver neural stimulation to the carotid sinus to control respiration.

FIG. 9 is a block diagram of portions of an example of an ambulatory medical device 900 to deliver neural stimulation to the carotid sinus to control respiration of a patient or subject. The ambulatory medical device 900 may be wearable or implantable.

The ambulatory medical device 900 includes a physiologic sensing circuit 905 and a control circuit 910. The physiologic sensing circuit 905 senses an electrical respiration signal representative of respiration of a subject. The control circuit 910 is communicatively coupled to the physiologic sensing circuit 905. The communicative coupling allows the control circuit 910 to communicate electrical signals with the physiologic sensing circuit 905 even though there may be intervening circuitry. The control circuit 910 can be a processor, a digital signal processor, application specific integrated circuit (ASIC), microprocessor, or other type of processor, interpreting or executing instructions in software modules or firmware modules. The control circuit 910 can include other circuits or sub-circuits to perform the functions described. These circuits may include software, hardware, firmware or any combination thereof. Multiple functions can be performed in one or more of the circuits as desired.

The respiration signal includes respiration information about the subject. The respiration signal can include any signal indicative of the respiration of the subject, such as inspiratory volume or flow, expiratory volume or flow, breath rate or timing, minute ventilation, a measure of Cheynes-Stokes breathing or periodic breathing, or any combination, permutation, or component of the respiration of the subject. The control circuit 910 includes a respiration monitor circuit 915 that extracts a respiration parameter from the respiration signal, and detects that a value of the respiration parameter is outside of a target value range for the respiration parameter. The control circuit 910 also includes a therapy circuit 920 that delivers neural stimulation to the carotid sinus of the subject to stimulate respiration and to adjust respiration to maintain the value of the respiration parameter within the target value range.

In some examples, the respiration monitor circuit 915 detects that the respiration parameter value satisfies an apnea detection threshold or other sleeping disordered breathing detection threshold. The control circuit 910 initiates delivery of neural stimulation to the carotid sinus in response to the respiration parameter satisfying the respiration apnea detection threshold. In some examples, the therapy circuit 920 delivers neural stimulation to a vagal nerve of the subject. The respiration monitor circuit 915 detects that the respiration parameter value satisfies a hyperpnea detection threshold, and the control circuit is configured to initiate delivery of neural stimulation to the vagal nerve of the subject to depress respiration of the subject. In this way, the ambulatory medical device 900 implements feedback control maintain respiration of a subject within specified parameters.

In certain examples, the respiration monitor circuit 915 detects that the respiration parameter value satisfies a hypopnea detection threshold, and the control circuit is configured to initiate delivery of neural stimulation to the carotid sinus in response to the respiration parameter satisfying the respiration hypopnea detection threshold. Thus, the ambulatory medical device 900 can prevent respiration of the subject from oscillating between episodes of hyperpnea and episodes of apnea or hypopnea.

According to some examples, the physiologic sensing circuit 905 includes a chemical sensing circuit that detects at least one of serum carbon dioxide or hydrogen ions (pH) in the bloodstream. The respiration parameter includes a sensed serum partial pressure of the at least one of carbon dioxide ($pCO_2$) or hydrogen ions (pH). The control circuit 910 initiates neural stimulation when the serum partial pressure is not within a target range for the partial pressure.

In some examples, the physiologic sensing circuit 905 includes a respiration sensing circuit. The respiration parameter includes at least one of a respiration rate of the subject, an inter-breath interval of the subject, a measure of variability of respiration rate of the subject, or a measure of variability of an inter-breath interval of the subject. In some examples, the extracted respiration parameter includes a measure of periodic breathing of the subject, and wherein the respiration monitor circuit is configured to detect Cheyne-Stokes breathing using the measure of periodic breathing.

In certain examples, the respiration sensing circuit can include an implantable impedance sensing circuit and the respiration signal may be a measured impedance signal. An example of an implantable impedance sensing circuit includes transthoracic impedance circuit. Transthoracic impedance can be sensed between an electrode on an implantable lead and an electrode formed on a housing of an IMD. An approach to measuring thoracic impedance is described in Hartley et al., U.S. Pat. No. 6,076,015 "Rate Adaptive Cardiac Rhythm Management Device Using Transthoracic Impedance," filed Feb. 27, 1998, which is incorporated herein by reference. The respiration parameter includes at least one of tidal volume or minute ventilation calculated for the subject. In certain examples, respiration monitor circuit 915 can extract respiration rate from the respiration signal and determine tidal volume from the measured impedance values of the respiration signal. Minute ventilation can then be calculated using the respiration rate and tidal volume as MV=RR× TV.

In certain examples, the respiration sensing circuit includes a motion sensing circuit (e.g., an accelerometer) that senses motion of the thoracic cavity of the subject. The respiration parameter includes a respiration rate of the subject. In certain examples, the respiration circuit includes a volume or flow sensor and the respiration parameter extracted from the respiration signal includes tidal volume or a measure of ventilation air flow.

In some examples, the ambulatory medical device 900 includes a posture sensing circuit 930 communicatively coupled to the control circuit 910. Examples of a posture sensor include a multi-axis accelerometer and a tilt switch. With a posture sensor, a medical device can detect whether a patient is in an upright position, a supine position, a prone position, on his or her left or right side, or if the patient is in a tilted position. In certain examples, the respiration parameter is monitored in association with determined posture. In this way, a measure of the respiration parameter (e.g., tidal volume) may only be compared to other measurements of the respiration parameter obtained when the subject is in the same known posture (e.g., laying on his or her left side).

According to some examples, the control circuit 910 includes a central apnea recognition circuit 925 that discriminates an episode of central apnea from an episode of obstructive apnea. In response to the respiration monitor circuit 915 detecting that the respiration parameter value satisfies an apnea detection threshold, the control circuit 910 initiates delivery of neural stimulation to the carotid sinus in response to the respiration parameter satisfying the respiration apnea detection threshold and the central apnea recognition circuit 925 identifying the respiration apnea as central apnea. In this way treatment of obstructive apnea by neural stimulation can be avoided. In some examples, the central apnea recognition circuit 925 recognizes central apnea from oscillations in the measured respiratory parameter. In some examples, the central apnea recognition circuit 925 recognizes central apnea from oscillations in breathing rate. In some examples, the central apnea recognition circuit 925 recognizes central apnea from oscillations in measured $pCO_2$.

As explained previously, patients with HF often exhibit some form of apnea or hypopnea and often exhibit Cheyne-Stokes respiration. Controlling respiration of HF patient with neural stimulation can improve hemodynamics of the HF patient.

Additional Notes and Examples

Example 1 includes subject matter (such as an apparatus) comprising a physiologic sensing circuit configured to sense an electrical respiration signal representative of respiration of a subject and a control circuit. The control circuit includes a respiration monitor circuit and a therapy circuit. The respiration monitor circuit is configured to extract a respiration parameter from the respiration signal and detect that a value of the respiration parameter is outside of a target value range for the respiration parameter. The therapy circuit is configured to deliver neural stimulation to the carotid sinus of the subject to stimulate respiration and to adjust respiration to maintain the value of the respiration parameter within the target value range.

In Example 2, the subject matter of Example 1 can optionally include a therapy circuit configured to deliver neural stimulation to a vagal nerve of the subject, a respiration monitor circuit configured to detect that the respiration parameter value satisfies a hyperpnea detection threshold, and a control circuit configured to initiate delivery of neural stimulation to the vagal nerve of the subject to depress respiration of the subject.

In Example 3, the subject matter of one or any combination of Examples 1 and 2 can optionally include a respiration monitor circuit configured to detect that the respiration parameter value satisfies a sleeping disordered breathing detection threshold, and a control circuit configured to initiate delivery of neural stimulation to the carotid sinus in response to the respiration parameter satisfying the sleeping disordered breathing detection threshold.

In Example 4, the subject matter of one or any combination of Examples 1-3 can optionally include a respiration monitor circuit configured to detect that the respiration parameter value satisfies at least one of an apnea detection threshold or a hypopnea detection threshold, and a control circuit configured to initiate delivery of neural stimulation to the carotid sinus in response to the respiration parameter satisfying the at least one of the apnea detection threshold or the hypopnea detection threshold.

In Example 5, the subject matter of one or any combination of Examples 1-4 can optionally include a respiration monitor circuit configured to detect that the respiration parameter value satisfies an apnea detection threshold, a control circuit that includes a central apnea recognition circuit configured to discriminate an episode of central apnea from obstructive apnea. The control circuit can optionally be configured to initiate delivery of neural stimulation to the carotid sinus in response to the respiration parameter satisfying the respiration apnea detection threshold and the central apnea recognition circuit identifying the respiration apnea as central apnea.

In Example 6, the subject matter of one or any combination of Examples 1-5 can optionally include a physiologic sensing circuit that includes a chemical sensing circuit configured to detect at least one of serum carbon dioxide or hydrogen ions (pH), and a respiration parameter that includes a sensed serum partial pressure of the at least one of carbon dioxide carbon dioxide or hydrogen ions (pH).

In Example 7, the subject matter of one or any combination of Examples 1-6 can optionally include a physiologic sensing circuit that includes a respiration sensing circuit, and the respiration parameter can optionally include at least one of tidal volume or minute ventilation calculated for the subject.

In Example 8, the subject matter of one or any combination of Examples 1-7 can optionally include a physiologic sensing circuit that includes a respiration sensing circuit. The respiration parameter can optionally include at least one of a respiration rate of the subject, an inter-breath interval of the subject, a measure of variability of respiration rate of the subject, or a measure of variability of an inter-breath interval of the subject.

In Example 9, the subject matter of one or any combination of Examples 1-8 can optionally include a physiologic sensing circuit includes a respiration sensing circuit, and the respiration parameter includes a measure of periodic breathing of the subject, and wherein the respiration monitor circuit is configured to detect Cheyne-Stokes breathing using the measure of periodic breathing.

In Example 10, the subject matter of one or any combination of Examples 1-9 can optionally include a respiration sensing circuit that includes an implantable impedance sensing circuit.

In Example 11, the subject matter of one or any combination of Examples 1-10 can optionally include a physiologic sensing circuit that includes a motion sensing circuit configured to sense motion of the thoracic cavity of the subject, and wherein the respiration parameter includes a respiration rate of the subject.

Example 12 can include subject matter (such as a method, a means for performing acts, or a machine-readable medium including instructions that, when performed by the machine, cause the machine to perform acts), or can optionally be combined with the subject matter of one or any combination of Examples 1-11 to include such subject matter comprising monitoring a respiration parameter of a subject using a medical device, detecting that a value of the respiration parameter is outside of a target value range for the respiration parameter, and delivering neural stimulation to the subject with the medical device to stimulate respiration and delivering neural stimulation to the subject to adjust respiration to maintain the value of the respiration parameter within the target value range. Delivering neural stimulation to the subject to stimulate respiration includes delivering neural stimulation to the carotid sinus of the subject.

Such subject matter can include a means for monitoring a respiration parameter, illustrative examples of which can include a physiologic sensing circuit, chemical sensing circuit, a respiration sensing circuit, an implantable impedance sensing circuit, a motion sensing circuit. Such subject matter can include a means for detecting that a value of the respiration parameter is outside of a target value range for the respiration parameter, illustrative examples of which can include a respiration monitor circuit. Such subject matter can include a means for delivering neural stimulation such as a therapy circuit.

In Example 13, the subject matter of Example 12 can optionally include detecting that the respiration parameter value satisfies a hyperpnea detection threshold, and stimulating a vagal nerve of the subject to depress respiration of the subject.

In Example 14, the subject matter of one or any combination of Examples 12 and 13 can optionally include detecting that the respiration parameter value satisfies a sleeping disordered breathing detection threshold, and stimulating a carotid sinus in response to the respiration parameter satisfying the sleeping disordered breathing detection threshold.

In Example 15, the subject matter of one or any combination of Examples 12-14 can optionally include detecting that the respiration parameter value satisfies a hypopnea detection threshold, and stimulating a carotid sinus in response to the respiration parameter satisfying the respiration hypopnea detection threshold.

In Example 16, the subject matter of one or any combination of Examples 12-15 can optionally include detecting that the respiration parameter value satisfies an apnea detection threshold, and stimulating the carotid sinus in response to the respiration parameter satisfying the respiration apnea detection threshold.

In Example 17, the subject matter of one or any combination of Examples 12-16 can optionally include discriminating between an episode of central apnea and an episode of obstructive apnea of the subject using the medical device, and stimulating the carotid sinus in response to the respiration parameter satisfying the respiration apnea detection threshold and identifying the respiration apnea as central apnea.

In Example 18, the subject matter of one or any combination of Examples 12-17 can optionally include monitoring a respiration parameter that includes a sensed serum partial pressure of carbon dioxide or hydrogen ion (pH).

In Example 19, the subject matter of one or any combination of Examples 12-18 can optionally include monitoring a respiration parameter that includes at least one of tidal volume or minute volume calculated for the subject.

In Example 20, the subject matter of one or any combination of Examples 12-19 can optionally include monitoring a respiration parameter that includes at least one of a respiration rate of the subject, an inter-breath interval of the subject, a measure of variability of respiration rate of the subject, or a measure of variability of an inter-breath interval of the subject.

Example 21 can include, or can optionally be combined with any portion or combination of any portions of any one or more of Examples 1-20 to include, subject matter that can include means for performing any one or more of the functions of Examples 1-20, or a machine-readable medium including instructions that, when performed by a machine, cause the machine to perform any one or more of the functions of Examples 1-20.

These non-limiting examples can be combined in any permutation or combination.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventors also contemplate examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An apparatus comprising:
   a physiologic sensing circuit configured to sense an electrical respiration signal representative of respiration of a subject; and a control circuit, wherein the control circuit includes:
a respiration monitor circuit configured to:
extract a respiration parameter from the respiration signal; and
detect that a value of the respiration parameter is outside of a target value range for the respiration parameter; and
a therapy circuit configured to deliver neural stimulation to one or more carotid baroreceptors at the carotid sinus of the subject to stimulate respiration and deliver neural stimulation to the vagal nerve to depress respiration to maintain the value of the respiration parameter within the target value range.

2. The apparatus of claim 1,
wherein the respiration monitor circuit is configured to detect that the respiration parameter value satisfies a hyperpnea detection threshold, and
wherein the control circuit is configured to initiate delivery of neural stimulation to the vagal nerve of the subject to depress respiration of the subject.

3. The apparatus of claim 1,
wherein the respiration monitor circuit is configured to detect that the respiration parameter value satisfies a sleeping disordered breathing detection threshold, and
wherein the control circuit is configured to initiate delivery of neural stimulation to the carotid sinus in response to the respiration parameter satisfying the sleeping disordered breathing detection threshold.

4. The apparatus of claim 1,
wherein the respiration monitor circuit is configured to detect that the respiration parameter value satisfies at least one of an apnea detection threshold or a hypopnea detection threshold, and
wherein the control circuit is configured to initiate delivery of neural stimulation to the carotid sinus in response to the respiration parameter satisfying the at least one of the apnea detection threshold or the hypopnea detection threshold.

5. The apparatus of claim 3,
wherein the respiration monitor circuit is configured o detect that the respiration parameter value satisfies an apnea detection threshold,
wherein the control circuit includes a central apnea recognition circuit configured to discriminate an episode of central apnea from obstructive apnea; and
wherein the control circuit is configured to initiate delivery of neural stimulation to the carotid sinus in response to the respiration parameter satisfying the respiration apnea detection threshold and the central apnea recognition circuit identifying the respiration apnea as central apnea.

6. The apparatus of claim 1,
wherein the physiologic sensing circuit includes a chemical sensing circuit configured to detect at least one of serum carbon dioxide or hydrogen ions (pH), and wherein the respiration parameter includes a sensed serum partial pressure of the at least one of carbon dioxide carbon dioxide or hydrogen ions (pH).

7. The apparatus of claim 1, wherein the physiologic sensing circuit includes a respiration sensing circuit, and wherein the respiration parameter includes at least one of tidal volume or minute ventilation calculated for the subject.

8. The apparatus of claim 7, wherein the respiration sensing circuit includes an implantable impedance sensing circuit.

9. The apparatus of claim 1, wherein the physiologic sensing circuit includes a respiration sensing circuit, and wherein the respiration parameter includes at least one of a respiration rate of the subject, an inter-breath interval of the subject, a measure of variability of respiration rate of the subject, or a measure of variability of an inter-breath interval of the subject.

10. The apparatus of claim 1, wherein the physiologic sensing circuit includes a respiration sensing circuit, wherein the respiration parameter includes a measure of periodic breathing of the subject, and wherein the respiration monitor circuit is configured to detect Cheyne-Stokes breathing using the measure of periodic breathing.

11. The apparatus of claim 1, wherein the physiologic sensing circuit includes a motion sensing circuit configured to sense motion of the thoracic cavity of the subject, and wherein the respiration parameter includes a respiration rate of the subject.

12. A method comprising:
monitoring a respiration parameter of a subject using a medical device;
detecting that a value of the respiration parameter is outside of a target value range for the respiration parameter; and
delivering neural stimulation to the subject with the medical device to stimulate respiration and delivering neural stimulation to depress stimulation to maintain the value of the respiration parameter within the target value range,
wherein delivering neural stimulation to the subject to stimulate respiration includes delivering neural stimulation to one or more carotid baroreceptors at the carotid sinus of the subject and delivering neural stimulation to depress stimulation includes delivering neural stimulation to a vagal nerve of the subject.

13. The method of claim 12,
wherein detecting that the respiration parameter is outside of a target respiration range includes detecting that the respiration parameter value satisfies a hyperpnea detection threshold.

14. The method of claim 12,
wherein detecting that the respiration parameter is outside of a target respiration range includes detecting that the respiration parameter value satisfies a sleeping disordered breathing detection threshold, and
wherein delivering neural stimulation to the subject includes stimulating a carotid sinus in response to the respiration parameter satisfying the sleeping disordered breathing detection threshold.

15. The method of claim 14,
wherein detecting that the respiration parameter is outside of a target respiration range includes detecting that the respiration parameter value satisfies a hypopnea detection threshold, and
wherein delivering neural stimulation to the subject includes stimulating a carotid sinus in response to the respiration parameter satisfying the respiration hypopnea detection threshold.

16. The method of claim 14,
wherein detecting that the respiration parameter is outside of a target respiration range includes detecting that the respiration parameter value satisfies an apnea detection threshold, and
wherein delivering neural stimulation to the subject includes stimulating the carotid sinus in response to the respiration parameter satisfying the respiration apnea detection threshold.

17. The method of claim 16, including:
discriminating between an episode of central apnea and an episode of obstructive apnea of the subject using the medical device, and wherein delivering neural stimulation to the subject includes stimulating the carotid sinus in response to the respiration parameter satisfying the respiration apnea detection threshold and identifying the respiration apnea as central apnea.

18. The method of claim 12, wherein the respiration parameter includes a sensed serum partial pressure of carbon dioxide or hydrogen ion (pH).

19. The method of claim 12, wherein the respirations parameter includes at least one of tidal volume or minute volume calculated for the subject.

20. The method of claim 12, wherein the respiration parameter includes at least one of a respiration rate of the subject, an inter-breath interval of the subject, a measure of variability of respiration rate of the subject, or a measure of variability of an inter-breath interval of the subject.

* * * * *